United States Patent [19]

Conran

[11] Patent Number: 5,725,490
[45] Date of Patent: Mar. 10, 1998

[54] ELASTIC WRIST BRACE WITH SUPPORT AND LONGITUDINALLY EXTENDING FASTENER

[75] Inventor: Sebastian Conran, London, England

[73] Assignee: Patricia Wyndham, Petersfield, England

[21] Appl. No.: 807,312

[22] Filed: Feb. 27, 1997

Related U.S. Application Data

[63] Continuation of Ser. No. 362,460, May 4, 1995, abandoned.

[30] Foreign Application Priority Data

Jul. 3, 1992 [GB] United Kingdom ............... 9214224

[51] Int. Cl.⁶ ........................ A61F 5/01; A61F 13/00
[52] U.S. Cl. ................................... 602/21; 602/64
[58] Field of Search ....................... 602/5, 6, 7, 9, 602/20, 21, 60, 64; 128/878, 879; 2/16, 17, 18, 19, 159–162, 170; D24/190

[56] References Cited

U.S. PATENT DOCUMENTS

| | | | |
|---|---|---|---|
| 1,469,315 | 10/1923 | Hansard | 602/21 |
| 1,750,183 | 3/1930 | Marinsky | 2/160 |
| 3,327,703 | 6/1967 | Gamm | 602/21 |
| 4,670,909 | 6/1987 | Forrester | 2/160 |
| 4,854,309 | 8/1989 | Elsey | 602/21 |
| 4,862,521 | 9/1989 | Mann | 2/160 |
| 4,868,927 | 9/1989 | Bourdeu et al. | 2/159 X |
| 5,160,314 | 11/1992 | Peters | 602/21 |

FOREIGN PATENT DOCUMENTS

| | | | |
|---|---|---|---|
| 2650176 | 2/1991 | France | 602/21 |
| 528044 | 1/1957 | Netherlands | 602/21 |
| 8601707 | 3/1986 | WIPO | 602/21 |

Primary Examiner—Richard J. Apley
Assistant Examiner—Kim M. Lee
Attorney, Agent, or Firm—Alix, Yale & Ristas, LLP

[57] ABSTRACT

A wrist brace comprises a sleeve adapted to extend from the hand region of the wearer to a forearm region of the wearer. The sleeve can be made from a material which is elastic in both the circumferential and longitudinal directions. The wrist brace further comprises a preformed support removably positioned within the sleeve. The support longitudinally extends along the sleeve in order to support the wearer's wrist. The sleeve is provided with a longitudinally extending fastening means which permits the brace to be fastened about the wearer's wrist by longitudinally operating a fastening member to thereby pull together portions of the sleeve material against its circumferential elasticity. Similarly, the brace can be removed from the wearer's wrist by longitudinally operating the fastening member to thereby release the portions of the sleeve material.

19 Claims, 2 Drawing Sheets

ELASTIC WRIST BRACE WITH SUPPORT AND LONGITUDINALLY EXTENDING FASTENER

This is a continuation of application application Ser. No. 08/362,460 filed on May 4, 1995, abandoned, which was the National Phase of International Application PCT/GB93/01395 filed on Jul. 5, 1993 and which designated the U.S..

BACKGROUND OF THE INVENTION

1. Field of the Invention

The present invention relates primarily to wrist braces and, in particular, but not exclusively to wrist braces for rheumatoid arthritics.

2. Description of the Related Art

Wrist braces are worn by rheumatoid arthritics to restrict movement of the wrist joint and are designed to support the wrist whilst still allowing the fingers and thumb the freedom to move. Although the brace substantially immobilizes the wrist, it is important that the fingers and thumb are still able to move freely so that the finger and thumb joints do not stiffen and the muscles weaken.

Wrist braces are not only worn by rheumatoid arthritics but may also be worn to support the wrist after injuries such as sprains and strains. Braces are also worn as orthopaedic supports, for example, after a wrist which has been broken is removed from a plaster cast. It has also been found that wrist braces are of benefit as a remedial aid to those suffering from repetitive strain injury which may occur, for example, from over use of a computer terminal. Finally wrist braces have been found to be of use by sportsmen and workmen in order to prevent injuries to the wrist occurring as a result of lifting heavy objects or weights.

One type of wrist brace which is currently widely available has a glove made of a material stretchable only in the longitudinal direction of the brace i.e. in the direction of the length of the arm. A metal support member is arranged to extend internally of the glove, from the palm, down the inside of the arm. The glove is adjusted to the individual wearer's requirements by adjustable fasteners arranged on the outside of the arm, i.e. on the side opposite to the support member. The fasteners usually take the form of a number of parallel releasable straps of e.g. VELCRO brand fastening straps which extend between opposed sides of glove material. In order to put the brace on, the straps are unfastened so that the hand can be inserted into the glove. The straps are then adjusted and fastened to accommodate the individual wearer's requirements.

However, the use of such straps has several disadvantages. The straps require a relatively large amount of force to be applied by the patient to undo the straps which is a problem for those patients with weakened joints and in particular those patients with rheumatoid arthritis in both hands. This problem is further exacerbated by the tendency of the straps to slip so that the straps must be undone and tightened several times during the day. This repeated exertion has been found actually to aggravate the problems suffered by the patient.

Another disadvantage of the known wrist brace is that the straps are arranged along the top of arm, i.e., opposed to the support member. While this does not cause problems for a healthy wearer of the brace, the extra twisting of the elbow joint required for handling the straps is undesirable for arthritics etc. as additional strain may be put on this joint. Furthermore, the straps snag on objects and are unsightly.

Finally, the known wrist brace described earlier is usually made of a material which is elastic only in the longitudinal direction of the glove and arm. The glove is then adjusted to the wearer's size, perpendicular to the longitudinal axis, by the use of the straps.

SUMMARY OF THE INVENTION

According to a first embodiment of the present invention, there is provided a wrist brace comprising a glove extendable across the wrist of a wearer, support means extending longitudinally in said glove for supporting the wrist and fastening means for allowing the hand to be inserted into said glove when said fastening means are open and for retaining the hand in said glove when said fastening means are closed, wherein said fastening means is in the form of a zip or like fastener extending longitudinally of said glove.

Thus, by using a zip the wearer does not have to continually adjust the fastening means as once the zip is closed, it will remain so until opened by the user. Furthermore, the zip can be easily opened and closed by pulling in the longitudinal direction without the patient having to exert undue force on the zip, in an outward direction. Another advantage of using a zip or the like, is that the brace can be easily machine washed with or without the support member in place. With the known wrist braces, it has not been possible to successfully wash the brace as the straps have tended to snag on other items during the washing process.

To further facilitate the opening and closing of the zip it is preferred that the zip have a large pull of such a shape that it can be easily grasped by an arthritic.

The zip is preferably large toothed as this reduces the effort required by the user to open and close the zip.

According to a second aspect of the present invention, there is provided a wrist brace comprising a glove adapted to extend from a hand region of a wearer to a forearm region, support means extending longitudinally in the glove for supporting the wrist and fastening means allowing the brace to be secured to and removed from the wrist of the wearer, wherein said fastening means is arranged to extend along the inside of the arm of the wearer.

By arranging the fastening means to be along the inside of the wearer's arm, the need for twisting of the elbow joint is avoided. Furthermore, the appearance of the article is improved as the fastening means will not normally be visible, and there will be a reduced tendency for snagging.

It will be appreciated that the fastening means may advantageously be in the form of a zip as described in relation to the first invention.

In general, the support means will also extend along the inside of the arm, typically from the forearm to the palm of the hand. The support will then be positioned between the zip—or other fastener—and the wearer. This will reduce any irritation that might be caused by unevenness of the fastening means, the support acting as a shield.

According to a third aspect of the present invention, there is provided a wrist brace comprising a glove for extending across a wrist of a wearer, support means arranged inside the glove and extending along at least part of the length of the glove for supporting the wrist and fastening means for allowing the insertion of the hand when in the open position and for securing the brace to said wrist when in the closed position, wherein the glove is of a material which is elastic in two, substantially perpendicular directions. In general, the two directions will be the longitudinal and the circumferential directions.

Thus, the fastening means themselves do not need to be adjustable in the circumferential direction whilst still allowing the wrist brace to be adaptable to the wrists of a number of different sized wearers. This feature is particularly advantageous when combined with the features of the first invention. With this combination it is possible to provide a wrist brace which is adjustable to the individual wearer's requirements and once in position the wearer does not need to further adjust the brace until it is to be taken off.

Features of the third aspect of the present invention may additionally or alternatively be combined with aspects of the second aspect of the present invention.

The glove is preferably of a double layer of material. This may provide smooth edges for the glove. This feature not only improves the appearance of the glove, but also makes it more comfortable for the wearer.

Preferably the glove is of LYCRA brand stretch material or a material having similar properties. LYCRA brand stretch material has a number of advantages over the material used in the known wrist brace described earlier. In particular it can be easily washed and the material is not stained. It is also light and able to breathe which makes it comfortable for the wearer. Furthermore, the material has a pleasing appearance. This is advantageous in that it has been found that some patients are reluctant to wear wrist braces especially in public and at social events which can have a detrimental effect on the wrist joint of an arthritic. Thus with a pleasing appearance, the wrist brace will be more attractive to the patient and hence likely to be worn more often.

Another advantage of using LYCRA brand stretch material is that it is a relatively non-abrasive fabric. As time progresses, arthritics skin becomes weak and sensitive and the material of known wrist braces are relatively abrasive. Materials other than LYCRA brand stretch material having a low abrasive properties can also be used if desired.

In certain embodiments, additional support for the wrist may be provided in the form of an extra layer of material around the wrist joint. This additional layer of material may be the same as the material of the rest of the glove or may be of a different grade or type of material. For example the material may be thicker or less elastic in order to provide more support for the wrist.

In all of the above mentioned embodiments of the present inventions, it is preferred that the support member be arranged in a pocket which extends along at least part of the length of the glove, along the inside of the arm. The pocket is preferably shaped to conform to the shape of the support member.

In one embodiment, the pocket of the wrist brace is substantially tubular and closed at one end. The support member is then inserted from the other end. A flap may be provided at the open end so as to close off the pocket to retain the member in position.

The support member is preferably of plastics material which has the advantage over metal in that it is lighter. Plastics also has the advantage that whilst the support is sufficiently rigid, it still retains a slight resiliency which make it more comfortable for the wearer. The support member may, for example, be of ABS and may be moulded using any suitable technique such as injection moulding, vacuum forming etc.

Furthermore, if the support member is of plastics it may be relatively easily adjusted so that the wrist is supported at the desired angle by using a hot air gun.

The support member may have a plurality of perforations arranged along its length and preferably in the region of the part of the support member which contacts the palm. These perforations allow perspiration to escape which makes it more comfortable for the wearer.

As mentioned earlier, in certain preferred embodiments, the support member may be arranged so as to lie between the arm of the wearer and the fastening means so as to act as a guard. Thus if the fastening means is in the form of a zip or the like, parts of the zip are prevented from pressing into the arm of the wearer.

The support member may have an elongate portion which extends along the inner arm of a wearer and an upper, wider portion on which the palm of the wearer rests. In other embodiments, the upper portion may be of a similar width to the elongate portion. The size of the upper portion may be selected in dependence on the degree of gripping required by the wearer. A smaller upper portion can make gripping an object easier as compared with a larger upper portion. Preferably the upper portion is cupped so as to provide a convex surface which conforms to the shape of the wearer's palm.

The elongate portion may have a concave cross-section so that it conforms to the contour of the inside arm. A widened portion may be provided on the elongate portion for additional strength, if required.

The upper portion may be angled relative to the elongate portion so as to hold the wrist at the desired angle. This angle may be in the region 30° to 45°. Thus the wrist cannot move any further forward than the angle defined by the supports but can move back, if possible. In this way, depending on the angle selected, the wrist is substantially immobilized.

Preferably, the support member is removable received in a pocket of the glove. Thus when the brace requires washing, the support member can be removed and the glove washed. It should be noted that the wrist brace can also be successfully washed with the support member in place, as discussed earlier.

Further aspects of the present invention include the provision of a support member for use in a wrist brace, having any or all of the features discussed above. For example, an embodiment of the invention disclosed herein consists of a support member for use as a wrist brace, comprising a plastics member which is sufficiently rigid to support the wrist but has a degree of resiliency, the member having a convex palm engaging portion and an elongate arm engaging portion of concave section, the two portions being angled with respect to each other.

It will further be appreciated that the various aspects referred to above may all be of use in contexts other than wrist braces, and for example in the context of supports for other points of the human or animal body. Furthermore, in some cases a rigid support member may not be necessary in all cases, and the elasticity of a glove or sleeve may be sufficient.

Accordingly, there are a number of further embodiments encompassed by this specification.

BRIEF DESCRIPTION OF THE DRAWINGS

A wrist brace which embodies some of the inventions will now be described with reference to the accompanying drawings in which.

DESCRIPTION OF THE PREFERRED EMBODIMENTS

Figure 1:
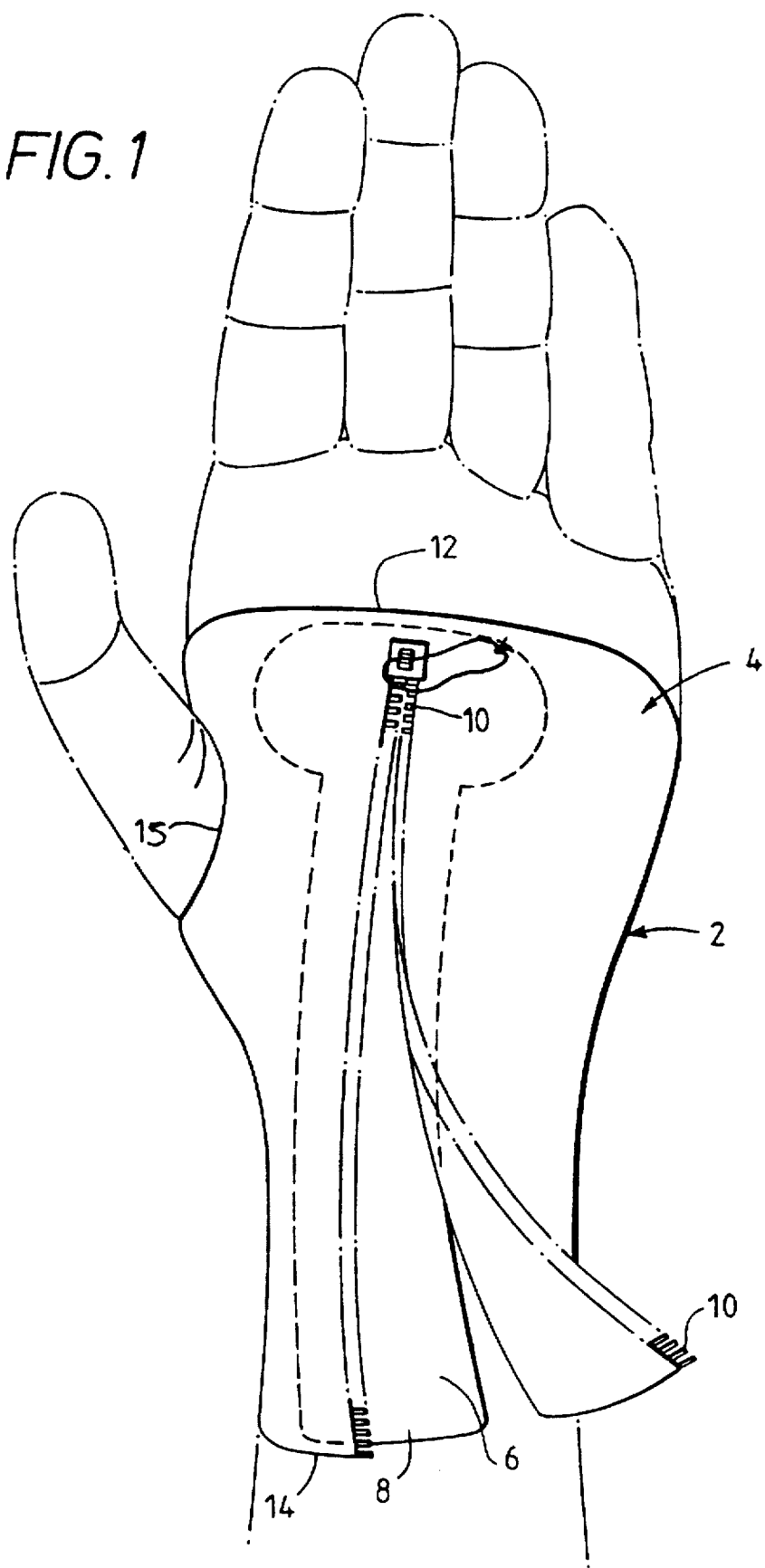
FIG. 1 shows a perspective view of a wrist brace as worn.
Figure 2:
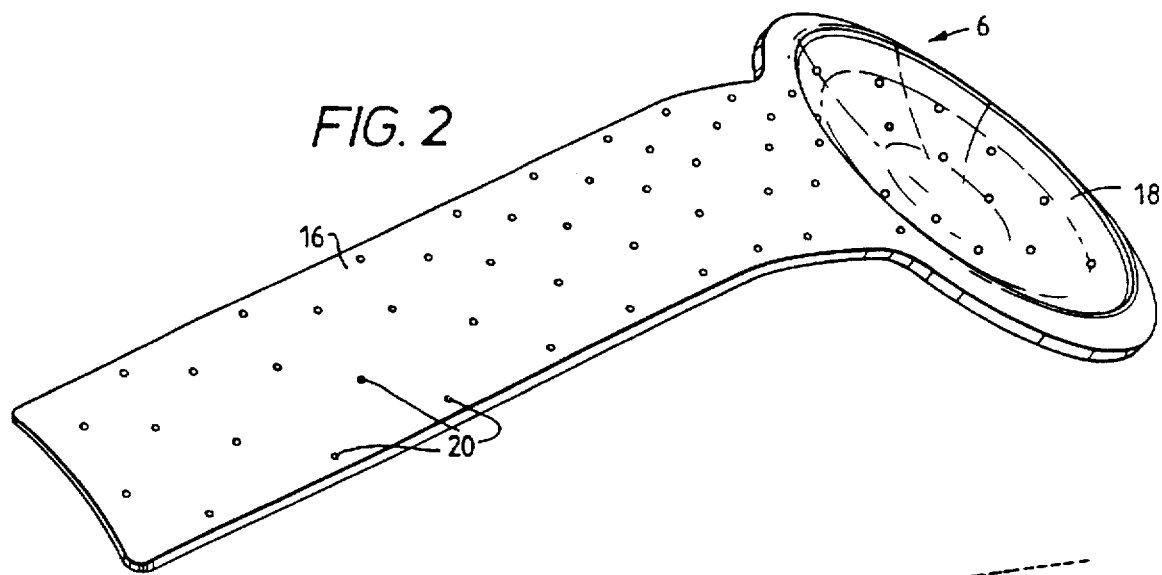
FIG. 2 shows a perspective view of a support member of FIG. 1.
Figure 3:
FIG. 3 shows a side view of the support member of FIG. 2.
Figure 4:
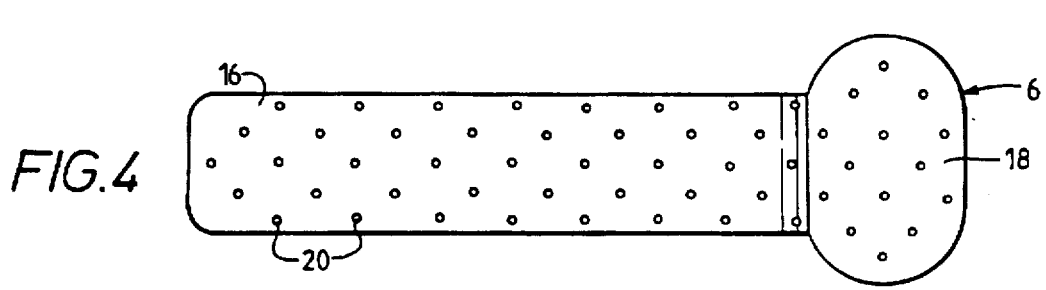
FIG. 4 shows a plan view of the support member of FIG. 2.

Referring first to FIG. 1, the wrist brace 2 comprises a glove or sleeve 4 inside of which is arranged a support member 6 (which can be seen more clearly in FIGS. 2 to 4). The support member 6 is arranged in a tubular pocket 8 which extends, internally along the length of the glove 4. Arranged above the support member 6 is a zip fastener 10 which extends along much of the length of the glove.

The various components of the wrist brace will now be described in more detail. The glove 4 is of a generally tubular shape and has openings 12 and 14 at opposed ends of the glove 4. At one end of the glove 4 is the opening 12 through which the fingers and upper part of the palm extend. The fingers of the wearer are thus able to move freely. The arm of the wearer extends through the other opening 14 of the glove 4. The glove 4 has an additional opening 15, adjacent the opening 12 for the fingers, for the thumb of the wearer. The glove 4 is made from a double layer of LYCRA brand stretch material or any other suitable material, and is stretchable in two perpendicular directions, i.e., along the glove and circumferentially of it.

As can be seen from FIGS. 2 to 4, the support member 6 has an elongate portion 16 and a cupped portion 18. The cupped portion 18 is shaped so as to conform generally to the shape of the part of the palm which rests against the cupped portion 18. The cupped portion 18 extends at approximately 30° to the longitudinal axis of the elongate portion 16 so that the wrist is prevented from being bent at an angle less than 30° relative to the extended position of the wrist. The elongate portion 16 is arranged so as to extend along the length of the arm and has, in the direction perpendicular to the length of the arm, a slightly concave cross-section so as to conform to the contour of the arm.

The support member 6 is made of a substantially rigid plastics material such as ABS but has a degree of resiliency. The support member has a number of through holes 20 through which the perspiration of the wearer can escape. The angle between the cupped portion and the elongate portion can be adjusted for a user by e.g. heating the plastic with a hot air gun, and bending it.

The support member 6 is arranged inside the glove 4 in tubular pocket 8. Pocket 8 is open at the end closest to the fingers and the support member 6 is inserted into the pocket 8, the other end of which is closed. The open end of the pocket has a flap (not shown) which is tucked over the open end of the pocket 8 to retain the support member 6 in place.

The pocket 8 and support member 6 are arranged so as to be below the zip 10 to provide protection to the user from any part of the zip which might otherwise press into the arm of the wearer. The zip 10 itself is of the type which has a large teeth to facilitate opening and closing. The zip also has a loop through which the fingers of the wearer can be inserted for opening and closing the zip 10.

Figure 5:
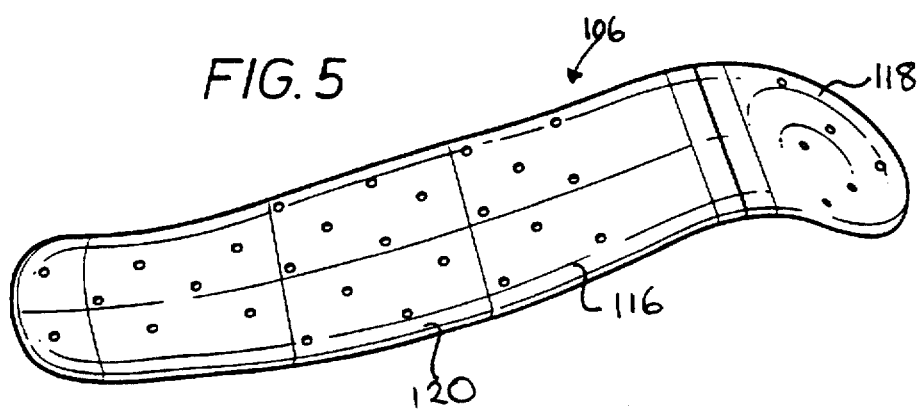
FIG. 5 shows a perspective view of an alternate support member for use in the wrist brace of FIG. 1.

FIG. 5 shows an alternate support member 106 which can be used in the wrist brace of FIG. 1. This alternate support member 106 is similar to that described earlier. However, support member 106 has a smaller cupped portion 118 which has a width similar to that of the elongate portion 116. If the cupped portion is too large the wearer can have difficulty in grasping objects. Accordingly, in some embodiments, such as shown in FIG. 5, the cupped portion is smaller. The elongate portion 116 has a widened portion 120 to increase the strength of the support member 106.

The following procedure is carried out in order to put on the brace having either of the support members illustrated. The zip 10 is moved to its opened position and the hand is inserted into the upper end of the glove 4 so that the fingers and thumb project from their respective openings 12, 14 and 15. The zip is then closed by pulling loop downwardly. Since LYCRA brand stretch material is stretchable in more than one direction, the brace is adjusted automatically to the size of the wearer. The brace needs no further adjustment until it has to be taken off when the above steps are carried out in reverse.

What is claimed is:

1. A wrist brace comprising a sleeve adapted to extend in a longitudinal direction from a hand region of a wearer to a forearm region, the sleeve being made from a material which is elastic in the circumferential and longitudinal directions, and a preformed support removably positioned in the sleeve, the support extending longitudinally of the sleeve for supporting the wrist of a wearer, wherein the sleeve is provided with a longitudinally extending zip fastening means permitting the brace to be fastened about the wrist of a wearer by pulling together portions of the sleeve material against its circumferential elasticity, or permitting the brace to be removed, the zip fastening means having a fastening member and being operated by movement of the fastening member in said longitudinal direction.

2. A wrist brace as claimed in claim 1 wherein the zip fastening means has a pull loop into which a digit of a user can be inserted.

3. A wrist brace as claimed in claim 2, wherein the sleeve is in the form of a glove having a wrist opening at one end, an opening for the fingers and an opening for the thumb at the other end, and a longitudinal opening extending from the wrist opening part way towards the fingers opening, the longitudinal opening being provided with said zip fastening means.

4. A wrist brace as claimed in claim 1, wherein the sleeve is in the form of a glove having a wrist opening at one end, an opening for the fingers and an opening for the thumb at the other end, and a longitudinal opening extending from the wrist opening part way towards the fingers opening, the longitudinal opening being provided with said zip fastening means.

5. A wrist brace as claimed in claim 1, wherein the support is positioned between said zip fastening means and the wearer.

6. A wrist brace as claimed in claim 5, wherein the support and zip fastening means are adapted to extend along the inside of the arm of the wearer.

7. A wrist brace as claimed in claim 6, wherein the support comprises an elongate portion and a cupped portion which provides a convex surface arranged to conform to the shape of a wearer's palm.

8. A wrist brace as claimed in claim 7, wherein the elongate portion of the support has a concave cross section which is arranged to conform to the inside of the arm of a wearer.

9. A wrist brace as claimed in claim 8, wherein the cupped portion is angled relative to the elongate portion at an angle in the range of 30 to 45 degrees.

10. A wrist brace as claimed in claim 9, wherein said zip fastening means has a pull loop into which a digit of a user can be inserted.

11. A wrist brace as claimed in claim 10, wherein the sleeve is in the form of a glove having a wrist opening at one end, an opening for the fingers and an opening for the thumb at the other end, and a longitudinal opening extending from the wrist opening part way towards the fingers opening, the longitudinal opening being provided with said zip fastening means.

12. A wrist brace as claimed in claim 11, wherein the support is perforated.

13. A wrist brace as claimed in claim 12, wherein the support is mounted within a pocket of the sleeve.

14. A wrist brace as claimed in claim 7 wherein the cupped portion is angled relative to the elongate portion at an angle in the range of 30 to 45 degrees.

15. A wrist brace as claimed in claim 1, wherein the support is perforated.

16. A wrist brace as claimed in claim 1, wherein the support is mounted within a pocket of the sleeve.

17. A wrist brace as claimed in claim 1, wherein the support is of plastics material and is sufficiently rigid to support the wrist whilst having a degree of resiliency.

18. A wrist brace for preventing excessive motion of a wearer's wrist while allowing motion of the fingers and thumb, comprising a sleeve of material extending in a longitudinal direction from a first opening at one end of the sleeve to a second opening at the other end of the sleeve, the sleeve being adapted to encircle the wrist and hand of the wearer in a circumferential direction, said material being elastic in both the longitudinal and circumferential directions, and a support being positioned in the sleeve, the first opening being for the wearer's fingers and part of the palm of the wearer's hand, the second opening being for the wearer's forearm and there being a third opening for the wearer's thumb, the brace also comprising longitudinally extending zip fastening means extending from the second opening to adjacent the first opening, along a region of the sleeve which, in use, overlies the palm of the wearer, the longitudinally extending zip fastening means having a fastening member and being operated by longitudinal movement of the fastening member to tighten the sleeve around the wearer's wrist against the circumferential elasticity of the sleeve material.

19. A wrist brace as claimed in claim 18, wherein the support extends along said longitudinal direction and is positioned between the zip fastening means and the inside of the sleeve.

* * * * *